US011900025B2

(12) United States Patent
Irizarry et al.

(10) Patent No.: US 11,900,025 B2
(45) Date of Patent: Feb. 13, 2024

(54) THEORETICAL MODELING AND MECHANISM OF DRUG RELEASE FROM CONTROLLED RELEASE IMPLANTS BY MICROSTRUCTURAL IMAGE CHARACTERIZATION

(71) Applicant: Merck Sharp & Dohme LLC, Rahway, NJ (US)

(72) Inventors: Roberto Irizarry, Wayne, PA (US); Antong Chen, Blue Bell, PA (US); Daniel Skomski, Yardley, PA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 915 days.

(21) Appl. No.: 16/291,553

(22) Filed: Mar. 4, 2019

(65) Prior Publication Data
US 2019/0371436 A1    Dec. 5, 2019

Related U.S. Application Data

(60) Provisional application No. 62/679,255, filed on Jun. 1, 2018.

(51) Int. Cl.
*G06F 30/20*    (2020.01)
(52) U.S. Cl.
CPC .................................. *G06F 30/20* (2020.01)
(58) Field of Classification Search
CPC ....................................................... G06F 30/20
See application file for complete search history.

(56) References Cited

U.S. PATENT DOCUMENTS

| | | | | | |
|---|---|---|---|---|---|
| 4,783,751 | A | * | 11/1988 | Ehrlich | G06V 20/695 |
| | | | | | 345/581 |
| 10,984,593 | B2 | * | 4/2021 | Wang | G06T 19/20 |
| 2017/0372470 | A1 | * | 12/2017 | Liu | G06T 7/60 |
| 2018/0296343 | A1 | * | 10/2018 | Wei | A61F 2/4455 |
| 2019/0108322 | A1 | * | 4/2019 | Zhang | G06T 7/11 |

FOREIGN PATENT DOCUMENTS

WO    WO-2015021424 A1 * 2/2015 ............. G01N 33/24

OTHER PUBLICATIONS

Brabant, Loes, Jelle Vlassenbroeck, Yoni De Witte, Veerle Cnudde, Matthieu N. Boone, Jan Dewanckele, And Luc Van Hoorebeke. "Three-dimensional analysis of high-resolution X-ray computed tomography data with Morpho+." Microscopy and Microanalysis 17, No. 2 (2011): 252-263 (Year: 2011).*

(Continued)

*Primary Examiner* — David A Hopkins
(74) *Attorney, Agent, or Firm* — Fenwick & West LLP

(57) ABSTRACT

Embodiments disclosed herein relate to a model for predicting the release profile of a controlled release device. The implant modeling system and models disclosed herein allow the accurate prediction of a release profile for a controlled release device based on features extracted from micro-resolution imagery. The models combine microstructural features that can be extracted at the XRCT resolution, including pore volume and connectivity, using erosion-dilation image analysis. This strategy allows prediction of release curves of the controlled release device using XRCT despite its resolution limitations.

20 Claims, 9 Drawing Sheets

(56) References Cited

OTHER PUBLICATIONS

Irizarry, et al. "Theoretical modeling and mechanism of drug release from long-acting parenteral implants by microstructural image characterization." Industrial & Engineering Chemistry Research 57, No. 45 (Oct. 17, 2018): 15329-15345 (Year: 2018).*
Wang, Yiwei, David F. Wertheim, Allan S. Jones, Hsin-I. Chang, and Allan GA Coombes. "Pharmaceutical Technology: Micro-CT Analysis of Matrix-Type Drug Delivery Devices and Correlation With Protein Release Behaviour." Journal of pharmaceutical sciences 99, No. 6 (2010): 2854-2862 (Year: 2010).*
Barman, Sandra Eriksson. The pore geometry of pharmaceutical coatings: statistical modelling, characterization methods and transport prediction. PhD Thesis, Chalmers Tekniska Hogskola (Sweden), 2020. 63 pages (Year: 2020).*
Vogel, H. J. "Morphological determination of pore connectivity as a function of pore size using serial sections." European Journal of Soil Science 48.3 (1997): 365-377. (Year: 1997).*
Rabbani, Arash, et al. "Evolution of pore-scale morphology of oil shale during pyrolysis: a quantitative analysis." Transport in Porous Media 119 (2017): 143-162. (Year: 2017).*
Pan, Chongxun, Markus Hilpert, and Cass T. Miller. "Pore-scale modeling of saturated permeabilities in random sphere packings." Physical Review E 64.6 (2001): 066702. (Year: 2001).*
Habel, "From experiments with images to 3D models", Chalmers University of Technology and University of Gothenburg. Göteborg, Sweden 2017 (Year: 2017).*
Al-Raoush, R. I., and C. S. Willson. "Extraction of physically realistic pore network properties from three-dimensional synchrotron X-ray microtomography images of unconsolidated porous media systems." Journal of hydrology 300.1-4 (2005): 44-64 (Year: 2005).*
Baldwin, Christopher A., et al. "Determination and characterization of the structure of a pore space from 3D volume images." Journal of colloid and interface science 181.1 (1996): 79-92. (Year: 1996).*
Beckingham, Lauren E. "Evaluation of macroscopic porosity-permeability relationships in heterogeneous mineral dissolution and precipitation scenarios." Water Resources Research 53.12 (2017): 10217-10230. (Year: 2017).*
Beckingham, Lauren E., et al. "2D and 3D imaging resolution trade-offs in quantifying pore throats for prediction of permeability." Advances in water resources 62 (2013): 1-12. (Year: 2013).*
Blunt, Martin J., et al. "Pore-scale imaging and modelling." Advances in Water resources 51 (2013): 197-216 (Year: 2013).*
Devaux, M. F., et al. "Particle size analysis of bulk powders using mathematical morphology." Powder Technology 90.2 (1997): 141-147 (Year: 1997).*
Diós, Péter, et al. "Influence of barium sulfate X-ray imaging contrast material on properties of floating drug delivery tablets." European Journal of Pharmaceutical Sciences 95 (2016): 46-53. (Year: 2016).*
Dong, H., P. Gao, and G. Ye. "Characterization and comparison of capillary pore structures of digital cement pastes." Materials and Structures 50 (2017): 1-12. (Year: 2017).*
Gostick, Jeff T., et al. "Pore network modeling of fibrous gas diffusion layers for polymer electrolyte membrane fuel cells." Journal of Power Sources 173.1 (2007): 277-290. (Year: 2007).*
Khanafer, K., and K. Vafai. "The role of porous media in biomedical engineering as related to magnetic resonance imaging and drug delivery." Heat and mass transfer 42.10 (2006): 939-953 (Year: 2006).*
Liang, Z., M. A. Ioannidis, and I. Chatzis. "Geometric and topological analysis of three-dimensional porous media: pore space partitioning based on morphological skeletonization." Journal of colloid and interface science 221.1 (2000): 13-24. (Year: 2000).*
Rabbani, Arash, and Shahab Ayatollahi. "Comparing three image processing algorithms to estimate the grain-size distribution of porous rocks from binary 2D images and sensitivity analysis of the grain overlapping degree." Special Topics & Reviews in Porous Media: An International Journal 6.1 (2015). (Year: 2015).*
Theile, T., and M. Schneebeli. "Algorithm to decompose three-dimensional complex structures at the necks: tested on snow structures." IET Image Processing 5.2 (2011): 132-140. (Year: 2011).*
Vogel, H. J., and K. Roth. "A new approach for determining effective soil hydraulic functions." European Journal of Soil Science 49.4 (1998): 547-556. (Year: 1998).*
Vogel, Hans-Jörg. "Topological characterization of porous media." Morphology of condensed matter: Physics and geometry of spatially complex systems. Berlin, Heidelberg: Springer Berlin Heidelberg, 2002. 75-92. (Year: 2002).*
Vogel, H-J., Ulrich Weller, and Steffen Schlüter. "Quantification of soil structure based on Minkowski functions." Computers & Geosciences 36.10 (2010): 1236-1245. (Year: 2010).*
Wang, Yiwei, et al. "Micro-CT in drug delivery." European journal of pharmaceutics and biopharmaceutics 74.1 (2010): 41-49 (Year: 2010).*
Wu, Yu San. Looking into tablets, characterization of pore structure in tablets using image analysis. Diss. Ph. D. Dissertation, Rijksuniversiteit Groningen, Amsterdam, 2008 (Year: 2008).*
Zha, Wenshu, et al. "A study of correlation between permeability and pore space based on dilation operation." Advances in Geo-Energy Research 1.2 (2017): 93-99 (Year: 2017).*
Higuchi, W. I., and Takeru Higuchi. "Theoretical analysis of diffusional movement through heterogeneous barriers." Journal of the American Pharmaceutical Association 49.9 (1960): 598-606. See the abstract and p. 599 (Year: 1960).*
Korte, Carolin, and Julian Quodbach. "3D-printed network structures as controlled-release drug delivery systems: dose adjustment, API release analysis and prediction." AAPS PharmSciTech 19 (2018): 3333-3342. See the abstract and pp. 3335-3339 (Year: 2018).*
Lemaire, V., J. Belair, and p. Hildgen. "Structural modeling of drug release from biodegradable porous matrices based on a combined diffusion/erosion process." International journal of pharmaceutics 258.1-2 (2003): 95-107. See the abstract and pp. 96-97 (Year: 2003).*
Saeio, Kiattisak, et al. "Factors influencing drug dissolution characteristic from hydrophilic polymer matrix tablet." Scientia Pharmaceutica 75.4 (2007): 147-164. See the abstract and pp. 155-158 (Year: 2007).*
Markl, Daniel, et al. "Characterisation of pore structures of pharmaceutical tablets: A review." International journal of pharmaceutics 538.1-2 (2018): 188-214. See the abstract and §§ 2-2.3 (Year: 2018).*
Siepmann, Juergen, and Nicholas A. Peppas. "Higuchi equation: Derivation, applications, use and misuse." International journal of pharmaceutics 418.1 (2011): 6-12. See the abstract and pp. 8, 10-11 (Year: 2011).*
Hassanzadeh, Parichehr, Fatemeh Atyabi, and Rassoul Dinarvand. "Ignoring the modeling approaches: Towards the shadowy paths in nanomedicine." Journal of Controlled Release 280 (2018): 58-75. See the abstract and § 3.3.2.3 (Year: 2018).*
Arifin, Davis Yohanes, Lai Yeng Lee, and Chi-Hwa Wang. "Mathematical modeling and simulation of drug release from microspheres: Implications to drug delivery systems." Advanced drug delivery reviews 58.12-13 (2006): 1274-1325. See the abstract and pp. 1277-1280 (Year: 2006).*
Young, Paul M., et al. "Microstructural analysis of porous composite materials: dynamic imaging of drug dissolution and diffusion through porous matrices." The AAPS journal 10 (2008): 560-564. See the abstract and p. 563 (Year: 2008).*
Huang, Xiaozhou, et al. "Quantitative three-dimensional analysis of poly (lactic-co-glycolic acid) microsphere using hard X-ray nanotomography revealed correlation between structural parameters and drug burst release." Journal of Pharmaceutical and Biomedical Analysis 112 (2015): 43-49. (Year: 2015).*
Al-Kharusi, A. S. et al., "Network extraction from sandstone and carbonate pore space images," Journal of Petroleum Science and Engineering, Apr. 2007, pp. 219-231, vol. 56, No. 4.

(56) References Cited

OTHER PUBLICATIONS

Auriault, J. L., "Effective macroscopic description for heat conduction in periodic composites," International Journal of Heat and Mass Transfer, Jun. 1983, pp. 861-869, vol. 26, No. 6.
Baghel, S. et al., "Polymeric Amorphous Solid Dispersions: A Review of Amorphization, Crystallization, Stabilization, Solid-State Characterization, and Aqueous Solubilization of Biopharmaceutical Classification System Class II Drugs," Journal of Pharmaceutical Sciences, Sep. 2016, pp. 2527-2544, vol. 105, No. 9.
Bekri, S. et al., "Dissolution of porous media," Chemical Engineering Science, Sep. 1995, pp. 2765-2791, vol. 50, No. 17.
Bhattad, P. et al., "Effect of Network Structure on Characterization and Flow Modeling Using X-ray Micro-Tomography Images of Granular and Fibrous Porous Media," Transport in Porous Media, Nov. 2011, pp. 363-391, vol. 90.
Blunt, M.J. et al., "Pore-scale imaging and modeling," Advances in Water Resources, Jan. 2013, pp. 197-216, vol. 51.
Costa, P. et al., "Modeling and comparison of dissolution profiles," European Journal of Pharmaceutical Sciences, May 2001, pp. 123-133, vol. 13, No. 2.
Dash, S. et al., "Kinetic Modeling on Drug Release from Controlled Drug Delivery Systems," Acta Poloniae Pharmaceutica-Drug Research, May 2010, pp. 217-223, vol. 67, No. 3.
Derby, J.J. et al., "A fully implicit method for simulation of the one-dimensional solidification of a binary alloy," 1986, Chemical Engineering Science, pp. 37-46, 41, vol. 41, No. 1.
Dong, H. et al., "Pore-network extraction from micro-computerized-tomography images," Physical Review E, Sep. 14, 2009, pp. 036307-1-036307-11, vol. 80, No. 3.
Ferrero, C. et al., "Towards elucidation of the drug release mechanism from compressed hydrophilic matrices made of cellulose ethers. III. Critical use of thermodynamic parameters of activation for modeling the water penetration and drug release processes," Journal of Controlled Release, Sep. 10, 2013, pp. 175-182, vol. 170, No. 2.
Haralick, R. M. et al., "Image Analysis Using Mathematical Morphology," IEEE Transactions on Pattern Analysis and Machine Intelligence, Jul. 1987, pp. 532-550, vol. PAMI-9, No. 4.
Hassani, B. et al., "A review of homogenization and topology optimization I-homogenization theory for media with periodic structure," Computers & Structures, Dec. 1998, pp. 707-717, vol. 69, No. 6.
Herrmann, S. et al., "Mechanisms controlling protein release from lipidic implants: Effects of PEG addition," Journal of Controlled Release, Apr. 2, 2007, pp. 161-168, vol. 118, No. 2.
Higuchi, T., "Rate of Release of Medicaments from Ointment Bases Containing Drugs in Suspension," Journal of Pharmaceutical Sciences, Oct. 1961, pp. 874-875, vol. 50, No. 10.
Irizarry, R., "An Artificial Chemical Process Approach for Optimization," Evolutionary Computation Journal, Dec. 2004, pp. 435-460, vol. 12, No. 4.
Jiang, Z. et al., "Efficient extraction of networks from three-dimensional porous media," Water Resources Research, Nov. 30, 2007, 17 pages, vol. 43, No. 12.
Jivkov, A. P. et al., "A novel architecture for pore network modelling with applications to permeability of porous media," Journal of Hydrology, Apr. 12, 2013, pp. 246-258, vol. 486.
Liu, M. et al., "High-resolution pore-scale simulation of dissolution in porous media," Chemical Engineering Science, Apr. 6, 2017, pp. 360-369, vol. 161.
Maniruzzaman, M. et al., "A Review of Hot-Melt Extrusion: Process Technology to Pharmaceutical Products," ISRN Pharmaceutics, Oct. 2012, 9 pages, vol. 2012, Article ID 436763.
Metzger, T. et al., "Influence of Pore Structure on Drying Kinetics: A Pore Network Study," AIChE Journal, Dec. 2007, pp. 3029-3041, vol. 53, No. 12.
Musiime, S. et al., "Adherence to Highly Active Antiretroviral Treatment in HIV-Infected Rwandan Women.," PLOS one, Nov. 2011, six pages, vol. 6, No. 11.
Okabe, H. et al., "Prediction of permeability for porous media reconstructed using multiple-point statistics," Physical Review E, Dec. 2004, pp. 066135-1-066135-10, vol. 70, No. 6.
Otsu, N., "A Threshold Selection Method from Gray-Level Histograms," IEEE Transactions on Systems, Man and Cybernetics, Jan. 1979, pp. 62-66, vol. SMC-9, No. 1.
Paul, D.R., "Elaborations on the Higuchi model for drug delivery," International Journal of Pharmaceutics, Oct. 10, 2011, pp. 13-17, vol. 418, No. 1.
Peng., S. et al., "Permeability estimation based on thin-section image analysis and 2D flow modeling in grain-dominated carbonates," Marine and Petroleum Geology, Nov. 2016, pp. 763-775, vol. 77.
Peppas, N.A. et al., "Mathematical models in drug delivery: How modeling has shaped the way we design new drug delivery systems," Journal of Controlled Release, Sep. 28, 2014, pp. 75-81, vol. 190.
Piri, M. et al., "Three-dimensional mixed-wet random pore-scale network modeling of two-and three-phase flow in porous media. I. Model description," Physical Review E, Feb. 4, 2005, pp. 026301-1-026302-30, vol. 71, No. 2.
Ramirez, G. et al., "Factors Affecting Adherence to Antiretroviral Therapy in People Living with HIV/AIDS," Journal of the Association of Nurses in AIDS Care, Jul./Aug. 2003, pp. 37-45, vol. 14, No. 4.
Schlüter, S. et al., "Image processing of multiphase images obtained via X-ray microtomography: A review," Water Resources Research, Apr. 2014, pp. 3615-3639, vol. 50, No. 4.
Siegel, R. A. et al., "A New Monte Carlo Approach to Diffusion in Constricted Porous Geometries," Journal of Colloid and Interface Science, Feb. 1986, pp. 426-440, vol. 109, No. 2.
Siegel, R. A. et al., "Mechanistic studies of macromolecular drug release from macroporous polymers. II. Models for the slow kinetic of slow release," Journal of Controlled Release, Oct. 1990, pp. 153-167, vol. 14, No. 2.
Siepmann, J. et al., "Modeling of diffusion controlled drug delivery," Journal of Controlled Release, Jul. 20, 2012, pp. 351-361. vol. 161, No. 2.
Siepmann, J. et al., "Higuchi equation: Derivation, applications, use and misuse," International Journal of Pharmaceutics, Oct. 10, 2011, pp. 6-12, vol. 418, No. 1.
Tenenbaum, J. B. et al., "A Global Geometric Framework for Nonlinear Dimensionality Reduction," Science, Dec. 22, 2000, pp. 2319-2323, vol. 290, No. 5500.
Tompson, A.F.B. et al., "Numerical Simulation of Solute Transport in Three-Dimensional, Randomly Heterogeneous Porous Media," Water Resources Research, Oct. 1990, pp. 2541-2562, vol. 26, No. 10.
Whetten, K. et al., "Trauma, Mental Health, Distrust, and Stigma Among HIV-Positive Persons: Implications for Effective Care," Psychosomatic Medicine, Jun. 2008, pp. 531-538, vol. 70, No. 5.
Wu, R. et al., "Two-phase flow with capillary valve effect in porous media," Chemical Engineering Science, Jan. 12, 2016, pp. 241-248, vol. 139, No. 12.
Xiong, Q. et al., "Review of pore network modeling of porous media: Experimental characterizations, network constructions and applications to reactive transport," Journal of Contaminant Hydrology, Sep. 2016, pp. 101-117, vol. 192.
Xiong, Q. et al., "Discrete modelling of contaminant diffusion in porous media with sorption," Microporous and Mesoporous Materials, Feb. 1, 2014, pp. 51-60, vol. 185.

* cited by examiner

THEORETICAL MODELING AND MECHANISM OF DRUG RELEASE FROM CONTROLLED RELEASE IMPLANTS BY MICROSTRUCTURAL IMAGE CHARACTERIZATION

CROSS REFERENCE TO RELATED APPLICATIONS

This application claims the benefit of U.S. Provisional Application No. 62/679,255, filed Jun. 1, 2018, which is incorporated by reference in its entirety.

TECHNICAL FIELD

This disclosure relates to the field of controlled release device design.

BACKGROUND

Controlled release devices releasing an active compound through diffusion have many applications both in the pharmaceutical industry and other industries. For example, a long-acting parenteral (LAP) medical implant for releasing an active pharmaceutical ingredient (API) over time. When designing a controlled release device, one consideration is the release profile of the controlled release device (describing the rate at which the active compound is released over time). For example, the release profile of a LAP implant can determine if the implant releases a therapeutic dose of the API and what the eventual lifespan of the implant would be. In some embodiments, the release profile of a controlled release device is determined in part by parameters of the manufacturing process used to generate the device which can be difficult to predict before a test controlled release device is manufactured.

Existing methods of determining release profile rely on performing an experimental determination of the release profile (for example, by measuring how much of the active compound is released over an expected lifespan of the device). However, this type of determination is time consuming and can require a long testing period for each potential update or improvement to the manufacturing process of the controlled release device.

SUMMARY

Embodiments disclosed herein relate to a method for estimating the release profile of a device for releasing a compound. An XRCT image of the device, which has particles of the compound to be released embedded in pores of a matrix, is received. Based on the XRCT image, pore volume and connectivity data for each of a set of pores of the device are determined. A model for estimating the release profile of the device based on the pore volume and connectivity is retrieved and used to estimate a release profile for the device based on the pore volume and connectivity data.

In some embodiments, the XRCT image is a voxel-based virtual 3D model of the device, where each voxel has sides of one micron.

In some embodiments, connectivity data for a pore is represented by a connectivity number representing a number of other pores the given pore is connected to.

In some embodiments, the model is a minimalistic model which determines the release profile of a device based on the pore volume and connectivity number for a set of pores.

In some embodiments, connectivity data for a pore is represented by a connectivity matrix identifying the other pores a given pore is connected to.

In some embodiments, the model is a network model simulating the release profile of the device based on the pore volume, the connectivity matrix, and a position for a set of pores.

In some embodiments, the pore volume and connectivity for a pore can be determined by generating an unlabeled mask from the XRCT image, where the unlabeled mask identifies a set of pores and the necks connecting pores, performing erosion and dilation operations on the unlabeled mask to remove the necks, resulting in disconnected pores which can then be labelled.

In some embodiments, the method includes constructing, based on the pore volume and connectivity data, and calibrating the model predicting the release profile of the device.

In some embodiments, one or more parameters of a process for manufacturing the device can be adjusted based on the estimated release profile.

In some embodiments, the device is a long-term release implant for releasing an active pharmaceutical ingredient.

In some embodiments, these methods may be implemented by a system including a XRCT imaging system and a device modelling system.

BRIEF DESCRIPTION OF THE DRAWINGS

Figure (FIG. 1A illustrates an example controlled release device, according to one embodiment.

DETAILED DESCRIPTION

Figures 1A, 1B:
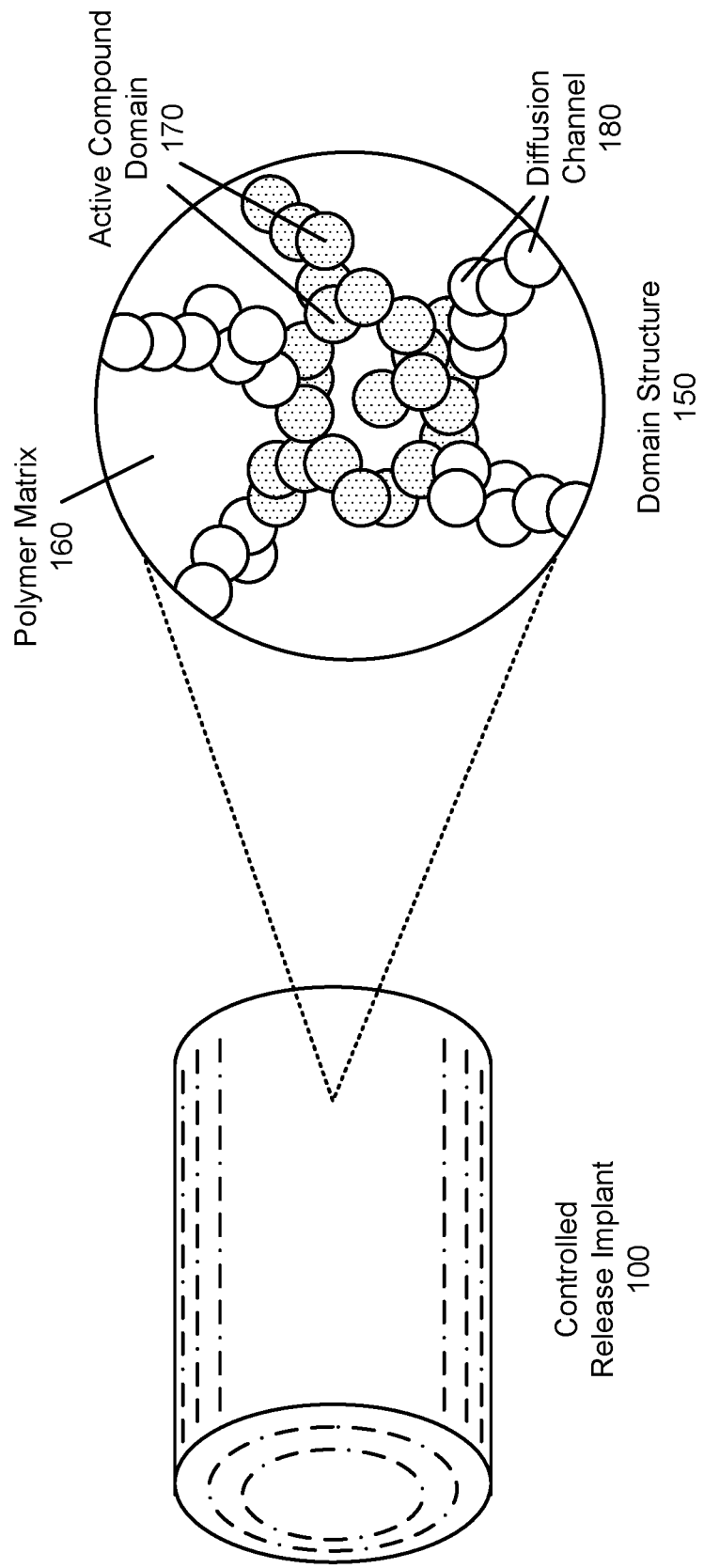
FIG. 1B illustrates a view of an example microdomain structure of a controlled release device, according to one embodiment.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

Overview

Embodiments disclosed herein relate to a model for predicting the release profile of a controlled release device including micron and/or submicron domains of an active compound distributed throughout a polymer matrix. In some embodiments, the active compound is not soluble in the polymer matrix. In such embodiments, the main release mechanism of the active compound from the controlled release device is diffusion of the active compound through channels that are formed within the polymer matrix as the active compound is dissolved. Thus, the performance of a controlled release device depends on the microstructure of the device. In turn, the microstructure of the device is influenced by the processing conditions used to manufacture the device.

Various embodiments of an implant modeling system and models disclosed herein allow the accurate prediction of a release profile for a controlled release device based on features extracted from micro-resolution imagery. For example, the disclosed implant modeling system and models can utilize x-ray computed tomography (XRCT) imagery to predict a release profile or other characteristics of a controlled release device based on microstructural features of the controlled release device.

The models combine microstructural features that can be extracted at the XRCT resolution, including pore volume and connectivity, using erosion-dilation image analysis. In some implementations, the models are calibrated based on experimental release profile data for a controlled release device. This strategy allows prediction of release curves of the controlled release device using XRCT despite its resolution limitations.

The described techniques for controlled release device modeling can have various advantages. Many laboratories have XRCT imaging systems capable of generating XRCT imagery with a maximum resolution of features of approximately one micron. However, the models previously used to predict release profile for a controlled release device rely on features (such as neck radius) with sub-micron sizes that are below the resolution of an XRCT imaging system and therefore cannot be accurately resolved. The models described herein may provide sufficiently accurate estimates of release profiles using features extracted from XRCT imagery. Therefore, enabling the use of existing XRCT equipment already available in laboratories to predict release profiles and other characteristics of a controlled release device. In other words, using such a model with an existing XRCT imaging system may improve the imaging system enabling it to perform a new function; the accurate prediction of release profiles for controlled release devices.

Controlled Release Devices

FIG. 1A illustrates an example controlled release device, according to one embodiment. In FIG. 1A, the controlled release device is a controlled release implant 100. A controlled release device as used herein is a device designed to release an "active compound" at a predictable rate, in some cases over an extended period of time. An active compound can be any compound desired to be released by the controlled release device, for example, an active pharmaceutical ingredient (API). Controlled release devices can be medical implants implanted in a patient to provide a constant dose of an API. The controlled release implant 100 is an example controlled release device which can be used to provide a constant dose of an API over a period of time (also known as a long-acting parenteral (LAP) formulation).

Controlled release devices can include particles of the active compound distributed throughout a polymer matrix. The polymer matrix can provide structure to the controlled release device, and may be made of any suitable material. For example, the polymer matrix may be ethylene vinyl acetate (EVA), polyurethane, polylactic acid (PLA), polycaprolactone (PCL), or the like. In some embodiments, the active compound is not soluble in the polymer matrix. In these embodiments, release of the active compound is accomplished by diffusion of the active compound through channels formed within the polymer matrix as the active compound is dissolved. In some embodiments, only the particles of the active compound connected to the exposed surface of the device (either directly or through a connected channel of the active compound) will be released. Therefore, the microdomain structure of a controlled release device, for example the size and distribution of particles/particle agglomerations ("domains") of the active compound and structure and positioning of the thin "necks" connecting the particles of active compound, can affect the release profile of the controlled release device. In some embodiments, characteristics of active compound domains can be measured by analysis of the cavities in the polymer matrix ("pores") created by the active compound domains.

FIG. 1B illustrates a view of an example microdomain structure 150 of the controlled release implant 100 shown in FIG. 1A, according to one embodiment. Note that a similar or identical microdomain structure 150 may be used for other types of controlled release device. As shown in FIG. 1B, the domain structure 150 of the controlled release implant 100 includes a polymer matrix 160 throughout which connected active compound domains 170 are embedded. In some embodiments, the active compound domains 170 on the surface of the controlled release implant 100 will be the first to diffuse, releasing the stored active compound. Over time, the voids left by the already released active compound domains will form diffusion channels 180, allowing the remaining active compound domains 170 deeper in the implant to be released. Features of the domain structure 150 can affect the release profile of the controlled release implant 100, according to some embodiments. For example, the size and connectivity of the active compound domains 170 (and therefore the resulting diffusion channels 180) can affect the release profile of the controlled release implant 100.

In some embodiments, the domain structure 150 is controlled in part by parameters of the manufacturing process used to produce the controlled release device. A manufacturing process, according to some embodiments, is a series of steps which can be followed to produce a controlled release device. In some embodiments, a controlled release device (for example, the controlled release implant 100) is manufactured using a hot melt extrusion (HME) process, for example using a process including extruding a preblended mix of polymer matrix and an active compound (for example, an API) through a heated extruder. Variations or changes in, for example, temperature, rate of extrusion, and ratio of active compound to polymer matrix (the "drug loading") in a HME manufacturing process can produce controlled release devices with different domain structures 150. Each change to the implant manufacturing process can produce a corresponding change to the domain structure 150, and therefore to the release profile of the eventual controlled release device.

As used herein, a "class" controlled release devices refers to a set of controlled release devices manufactured using a similar manufacturing process. Each controlled released device of a class of controlled release devices may have the same active compound and polymer matrix and, in some embodiments, is manufactured using the same general manufacturing process (such as HME). Within a class of controlled release devices there can be variation in microdomain structure (such as the domain structure 150) and release profile or other characteristics due to changes in the parameters of the manufacturing process. For example, a class of controlled release implants 100 manufactured using HME may contain controlled release implants 100 with different properties due to changes in the drug loading or extruder temperature for the HME process. In some embodiments, multiple controlled release devices of the same class are tested to find an optimized manufacturing process for a certain application. For example, a manufacturing process for controlled release implants 100 may be optimized to achieve a target release profile for providing a therapeutic dose of API without over- or under-dosing a patient.

Implant Modeling System

Figure 2:
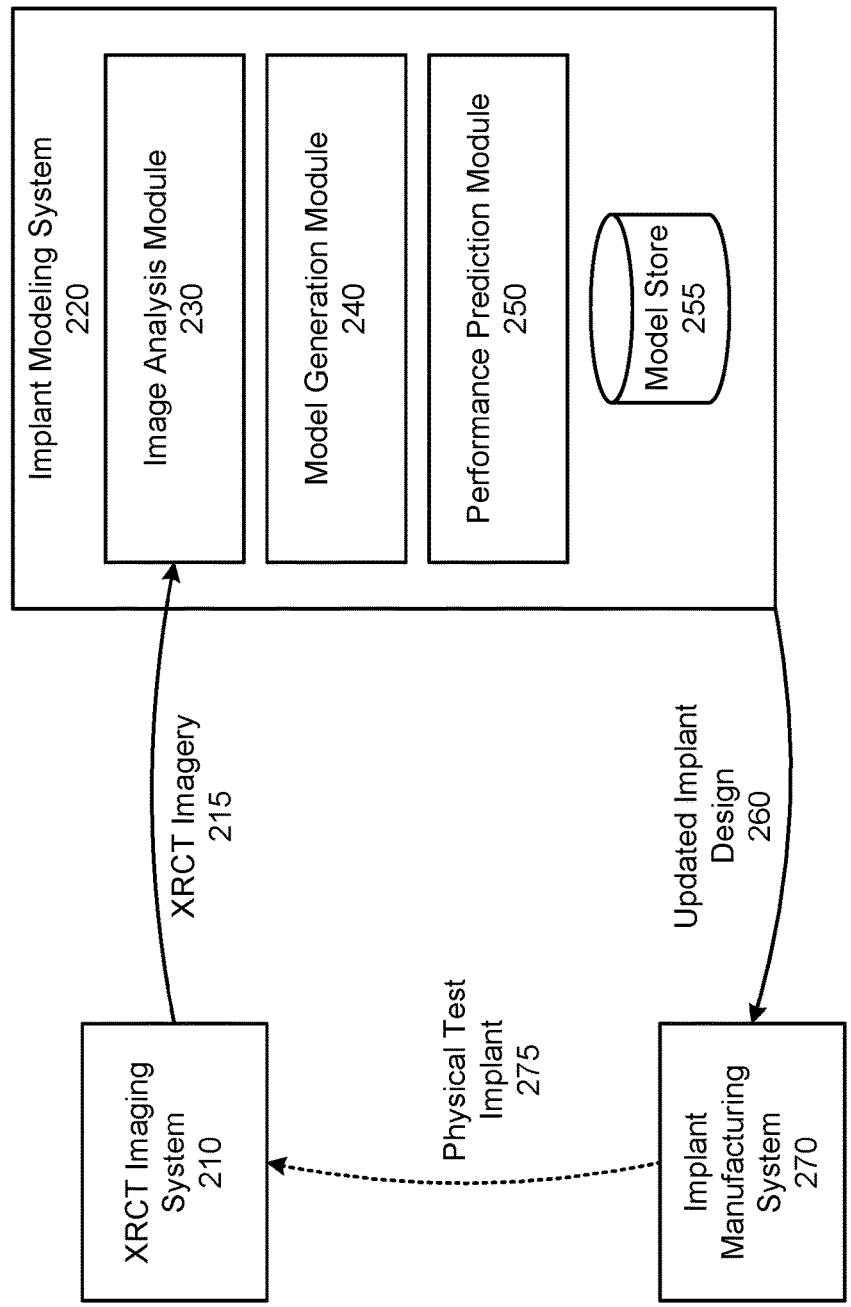
FIG. 2 is a block diagram illustrating an example environment in which an implant modeling system operates, according to one embodiment.

FIG. 2 is a block diagram illustrating an example environment in which an implant modeling system operates, according to one embodiment. The environment 200 of FIG. 2 includes an XRCT imaging system 210 which can produce XRCT imagery 215 of a controlled release device, an implant modeling system 220, in this embodiment including an image analysis module 230, a model generation module 240, a performance prediction module 250, and a model store 255, an updated implant design 260 for a controlled release device, and an implant manufacturing system which can manufacture a physical test implant 275 according to a manufacturing process. In other embodiments, the implant modeling system 220 can include additional, fewer, or different modules or stores than the ones depicted in FIG. 2. For example, the functions of multiple modules may be combined into one module, or the functions of one module may be split across multiple modules.

The XRCT imaging system 210 is a system capable of generating XRCT 215 imagery of a controlled release device. XRCT (also known as micro-computed tomography or microCT) techniques can operate with a resolution of approximately one micron (micrometer), referred to herein as "microscale" to distinguish from the "nanoscale" resolution required to distinguish sub-micron features. To generate XRCT imagery 215, the XRCT imaging system 210 can image the controlled release device in a series of cross-sectional slices, which are assembled to generate a virtual 3D model of the controlled release device, according to some embodiments. In some implementations, the XRCT imagery 215 differentiates between areas of the controlled release device containing the polymer matrix and areas containing the active compound. The resulting XRCT imagery 215 can have a resolution of approximately one micron (micrometer) and include a virtual 3D model of all or part of the imaged controlled release device. In other embodiments, a suitable virtual 3D model of an image controlled release device can be generated using any alternative technology. According to some implementations, the virtual 3D model of a controlled release device generated by the XRCT imaging system 210 is made of voxels with sides of approximately one micron, where each voxel is associated with an intensity. Once generated, the XRCT imagery 215 can be sent to the implant modeling system 220 for analysis of the controlled release device.

The implant modeling system 220 uses XRCT imagery 215 of a controlled release device to predict the release profile and/or other characteristics of the controlled release device. In some embodiments, the implant modeling system 220 can extract features from the received XRCT imagery 215 of a controlled release device, then generate and calibrate (if needed) a model of the controlled release device based on the extracted features. Once generated and calibrated, the implant modeling system 220 stores the model of the controlled release device is stored in the model store 225 for use, according to some embodiments. As described above, each controlled release device can be associated with a class of controlled release devices, and the stored model can be associated with a class.

Using a stored model for the controlled release device (or a previously stored model for an appropriate class of controlled release devices) the implant modeling system 220 can predict the release profile or other characteristics of a controlled release device. In some implementations, an updated implant design 260, for example outlining an updated manufacturing process for the controlled release device, is generated based on the predicted characteristics of the controlled release device. For example, changes can be implemented to improve the performance of the controlled release device, for example to achieve a desired release profile or lifespan for the controlled release device. In other implementations, the predicted characteristics are provided to one or more users of the implant modeling system 220.

The implant modeling system 220 can be connected to the XRCT imaging system 210 and/or otherwise receive XRCT imagery 215 by any suitably method. For example, the implant modeling system 220 can be connected to the XRCT imaging system 210 by a wired or wireless network, or may be integrated into the same device or system. Similarly, the implant modeling system 220 can be connected to the implant manufacturing system 270 by any suitable method including a wired or wireless network.

In some embodiments, the implant manufacturing system 270 generates controlled release devices based on a design of a specific controlled release device. The implant manufacturing system 270 can be any suitable small-scale or large-scale manufacturing system using any suitable manufacturing process to manufacture controlled release devices. As described above, some embodiments of the implant manufacturing system 270 use a HME process to generate controlled release devices. In some implementations, the microstructure of the manufactured controlled release device depends on one or more process-specific parameters of the manufacturing process. For example, a HME process can have parameters of extruder temperature, ratio of polymer matrix to active compound (drug loading), and the like, each of which may affect the microstructure of the resulting controlled release device. In embodiments using other suitable manufacturing processes, a design can specify other suitable parameters affecting the microstructure of the controlled release device. In some embodiments, the implant manufacturing system 270 can produce multiple variations of a controlled release device within the same class by varying one or more parameters of the manufacturing process according to a design of the controlled release device. The implant manufacturing system can adjust the parameters of a manufacturing process according to a received design (such as the updated implant design 260) and produce a physical controlled release device (such as the physical test implant 275).

As described above, changes to the manufacturing process can have an effect on the microstructure of the resulting controlled release device, but it is difficult to predict the exact changes (both to the microstructure and the performance of the controlled release device) a specific change to the manufacturing process will cause. Therefore, a physical test implant 275 manufactured based on the updated implant design 260 can be imaged by the XRCT imaging system 210 and the resulting XRCT imagery analyzed by the implant modeling system 220. In some implementations, this cycle of generating a test controlled release device by the implant manufacturing system 270, imaging by the XRCT imaging system 210, and analysis by the implant modeling system 220 to update the design of the controlled release device can be repeated until the controlled release device meets desired performance characteristics. In some implementations, subsequent revisions of an original controlled release device are in the same class as the originally controlled release device and can therefore utilize a stored model for the original controlled release device. As described above, when a stored model (for example, stored in the model store 255) exists for a class of controlled release device, the model can be applied to other controlled release devices in the class based on XRCT imagery 215, therefore reducing the iteration time when refining the design of a controlled release device, according to some embodiments. Once the controlled release device design is finalized, further controlled release devices based on the design can be manufactured at the implant manufacturing system 270 or at a suitable manufacturing facility using the determined manufacturing process. In some implementations, the implant modeling system 220 and XRCT imaging system 110 can be used for quality control of manufactured controlled release devices.

The image analysis module 230, according to some embodiments, analyzes and extracts features from XRCT imagery of a controlled release device. For example, the image analysis model can receive the XRCT imagery 215 from the XRCT imaging system 210. In some implementations, the image analysis module 230 receives raw XRCT data or a virtual 3D model of the controlled release device (such as in the XRCT imagery 215), but in other implementations but some or all of the functions of the image analysis module 230 can occur at the XRCT imaging system 210.

The image analysis module 230 can first generate an active compound mask by segmenting a received 3D model of the controlled release device into active compound, polymer matrix, and "background" (for example, the empty space outside the controlled release device). In some implementations, each voxel of the 3D model of the controlled release device is segmented based on the intensity of the voxel (where the highest intensity range is classified as active compound, a medium intensity range is classified as polymer matrix, and the remaining low intensity voxels classified as background).

Figure 4:
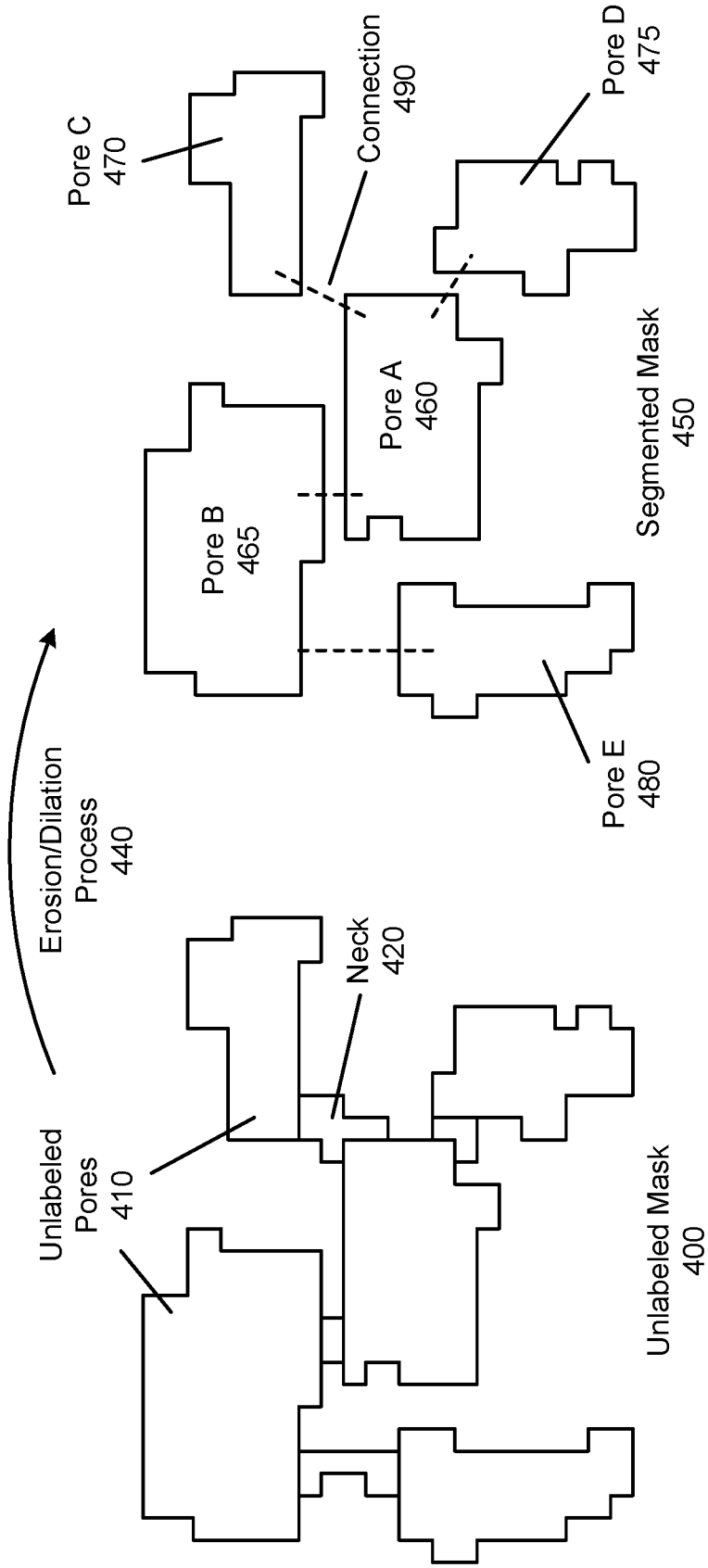
FIG. 4A illustrates an example active compound mask generated based on XRCT imagery, according to one embodiment.
FIG. 4B illustrates an example active compound mask processed to label distinct pores, according to one embodiment.

FIG. 4A illustrates an example a 2D cross section of an active compound mask generated based on XRCT imagery, according to one embodiment. The unlabeled mask 400 of FIG. 4A is an example active compound mask as generated based on XRCT imagery. The unlabeled mask 400 includes a plurality of unlabeled pores 410 of active compound connected by thin necks 420, each with a diameter of one to two voxels. In some implementations, the initially generated active compound mask is unlabeled and does not differentiate between different pores or between a pore and a neck.

As described above, the necks are below the resolution of the XRCT imaging system 210 and in some embodiments cannot accurately be represented by one-micron voxels (as significant fluctuations in the size of a neck would not change the number of voxels the neck is represented by).

In some implementations, the image analysis module 210 can label the unlabeled mask 400 using an erosion/dilation process 440 to segment the unlabeled mask 400 into disconnected pores which can then be labeled. The unlabeled mask can first be eroded until the necks 420 have been eroded away, leaving the unlabeled pores 410 disconnected from each other (albeit at a smaller size). Next the eroded mask can be labeled using 3D connected component analysis (or any other suitable labeling algorithm) and subsequently dilated to return the unlabeled pores 410 to their approximate original size. In some embodiments, an erosion amount of three voxels is used to remove the necks 420 (with a corresponding dilation of three voxels to return the unlabeled pores 410 to their original size), although any other suitable amount of erosion/dilation can be used. In other embodiments, a maximal ball algorithm can be used to segment and label the active compound mask.

In some implementations, applying the erosion/dilation process 440 to an unlabeled mask 400 produces a segmented mask 450. FIG. 4B illustrates an example a 2D cross section of an example active compound mask processed to label distinct pores, according to one embodiment. The segmented mask 450 of FIG. 4B includes a plurality of labeled pores 460-480 connected by connections 490. The connections 490 can be generated by the image analysis module 230 using any suitable technique, for example based on proximity between pores 460-480 (where pores in close proximity are assumed to be connected) or based on analysis of the unlabeled mask 400 and the labeled pores 460-480 of the segmented mask 450. In some embodiments, connections for a pore can be determined by searching in a region defined by a dilated version of the pore (in some cases, minus the original pore in the segmented mask 450) for any voxel associated with another pore 460-480 of the segmented mask 450. For example, to detect connections of pore A 460 the image analysis module 230 can search for voxels associated with other pores 465-480 inside a version of pore A 460 dilated using a structure element, such as a cube with sides of 3 voxels, but outside the original pore A 460. In this case, voxels associated with pores B, C, and D 465-475 may be detected within the search region and determined to be connected to pore A 460. In some implementations, the number of connections detected for each pore is stored, while in other embodiments the segmented mask 450 stores connections 490 between one or more pores 460-480.

In some embodiments, an erosion operation may be applied to a binary mask of an active pharmaceutical ingredient (API). By performing the erosion operations, necking regions of two voxels or less are removed. For the eroded binary mask, a 3D connected component analysis may be performed such that the disconnected pieces are identified and labeled. Based upon the labeled mask, a series of morphological dilation operations may be applied to recover the API domain approximately to its original size (e.g., enlarging previously unlabeled pores). The reconstructed and labeled mask can be obtained through the dilation operations.

Figure 5:
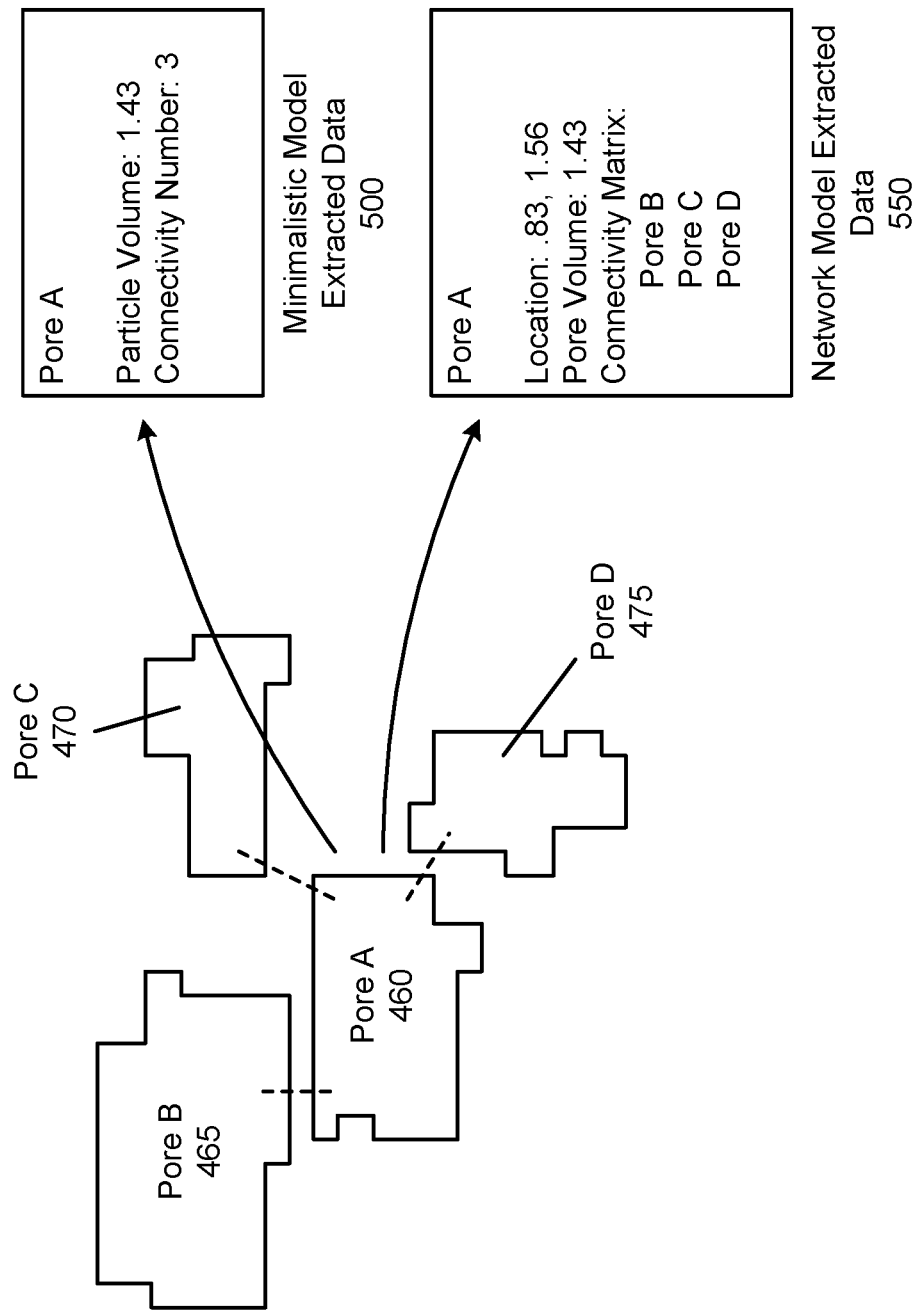
FIG. 5 illustrates data extracted from XRCT imagery to generate minimalistic or network models of a controlled release device, according to one embodiment.

Based on the segmented mask 450, the image analysis module 230 can extract a set of features for the generation or application of a model. FIG. 5 illustrates data extracted from XRCT imagery to generate minimalistic or network models of a controlled release device, according to one embodiment. FIG. 5 shows example minimalistic model extracted data 500 and network model extracted data 550 about pore A 460 of the segmented mask 450. In some embodiments, features can be extracted from each pore (for example, the pores 460-480) of the segmented mask 450. Extracted features of a pore can include a pore volume or pore size (e.g., measured in voxels), a pore location (e.g., coordinates of the center of mass of the pore), and a measure of connectivity of the pore. The measure of connectivity of a pore represents the connections between the pore and other nearby pores. In one embodiment, connectivity is measured as a "connectivity number" or "coordination number" (as included in the minimalistic model extracted data 500) noting the number of connections the pore has, but not which pore it is connected to. For example, pore A 460 is connected to pores B, C, and D 465-475, resulting in a connectivity number of 3. In another embodiment, the connectivity of a pore can be represented by a connectivity matrix (as included in the network model extracted data 550) listing the connected pores. For example, returning to the example of pore A 460, the resulting connectivity matrix would include an identifier for the connected pores B, C, and D 465-475. The use of these features to generate or apply minimalistic and/or network models will be discussed further below. FIG. 5 will be further discussed below.

Returning to FIG. 2, the model generation module 240 can generate a model of a controlled release device based on the features extracted by the image analysis module 230. In some implementations, the model generation module 240 uses experimental data from a controlled release device to calibrate an initial model which can then be stored and applied to predict performance for that controlled release device and other devices in the same class. Generated and/or calibrated models can be stored in any suitable location, for example the model store 255 of the implant modeling system 220. The models generated by the model generation module 240, according to some embodiments, can predict a release curve for the controlled release device (for example, by determining a release coefficient k or effective diffusivity coefficient $D_{\mathit{ff}}$) or other suitable characteristics of the controlled release device. The model generation module 240 and generating and calibrating models will be discussed further below in relation to FIG. 3.

The performance prediction module 250 can apply a stored model to predict the release profile or other characteristics of a controlled release device. For example, the performance prediction module 250 can apply a stored model (for example, from the model store 255) based on extracted features from XRCT imagery 215 of a controlled release device to predict the release profile of the controlled release device. As described above, the performance prediction module 250 can apply any suitable model to predict the performance of a controlled release device, including models generated and calibrated based on that specific controlled release device and models associated with a controlled release device of the same class (or associated with the class itself). In some implementations, the performance prediction module 250 uses pre-calibrated models retrieved from the model store 255 and does not require experimental release data to apply a model to the extracted features from XRCT imagery.

The model store 255, according to some embodiments, stores models generated by the model generation module 240 for later access and use (for example, by the performance prediction module 250). For example, models can be stored as one or more equations, as a set of calibration coefficients, or in any other suitable format. Models in the model store 255 can be associated with any suitable information, for example, a class of controlled release device, and indicator of a specific controlled release device used to generate the model, details or parameters of a manufacturing process for a controlled release device, a log of past uses of the model, XRCT data or extracted features used to generate the model (or from previous applications of the model), experimental calibration data used to calibrate the model, or any other suitable information.

Controlled Release Device Models

Figure 3:
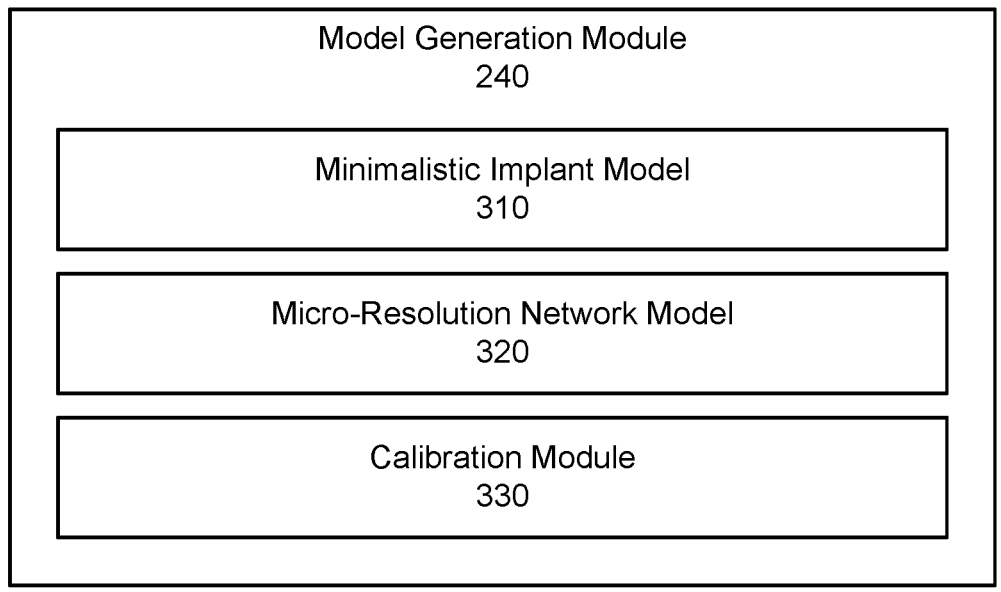
FIG. 3 is a block diagram illustrating an example model generation module, according to one embodiment.

FIG. 3 is a block diagram illustrating an example model generation module, according to one embodiment. As described above, the model generation module 240 can generate a model for a controlled release device based on features extracted from captured XRCT imagery. The model generation module 240 of FIG. 3 includes a minimalistic implant model 310, a micro-resolution network model 320, and a calibration module 330, although other embodiments of a model generation module 240 may include different or fewer submodules. In the embodiment of FIG. 3, the minimalistic implant model 310 and the micro-resolution network model 320 can each construct a model capable of predicting a release profile (or other suitable characteristics) of a controlled release device. As described above, each generated model is calibrated using experimental data, according to some embodiments. In some implementations, the model generation module 240 includes only one of the minimalistic implant model 310 or the micro-resolution network model 320 which is used to generate models of controlled release devices. For example, an implant modeling system 220 may use the minimalistic implant model 310 to generate a model for a controlled release device and calibration module 330 to calibrate the resulting model.

A minimalistic model (herein referring to a model constructed by the minimalistic implant model 310) can predict the release profile of a class of controlled release devices based on an idealized geometry, providing a convenient means of extracting relevant features to the release profile, according to some embodiments. A constructed minimalistic model can use pore volume and connectivity number data for a plurality of pores of a controlled release device to predict the release profile for the controlled release device. In some embodiments, the minimalistic models constructed by the minimalistic implant model 310 are not minimalistic in absolute terms but relative to previous methods of predicting release profile. For example, previous methods for determining release profile relied on experimentally mapping the release profile or required the use of additional features (such as neck radius) not used by the minimalistic model.

As shown in FIG. 5, the minimalistic model extracted data 500 can include a pore volume and connectivity number for each pore 460-480 of the segmented mask 450. In some implementations, the minimalistic model is described herein assuming a cylindrical and radially symmetrical controlled release device (such as the controlled release implant 100), however other shapes and configurations of controlled release device can be modeled using similar methods in other embodiments.

In some implementations, the minimalistic model predicts a release coefficient k for a Higuchi-type release relating the percentage of the active compound released W(t) to the square root of time.

$$W(t)=k\sqrt{t} \quad (1)$$

The minimalistic implant model 310 can determine k based on a linear correlation between k and a parameter $Z_{XRCT}$ computed based on the extracted XRCT imagery and the calibration coefficients a, b, α, and β.

$$k = a Z_{XRCT}(\alpha, \beta) + b \qquad (2)$$

$Z_{XRCT}$ can be associated with an effective diffusivity coefficient $D_{\!f\!f}$, according to some embodiments. In some embodiments, $Z_{XRCT}$ is determined based on the set of pore volumes V and coordination numbers $n_c$ as shown in equation 3.

$$Z_{XRCT}(\alpha, \beta) = \int_{V_{min}}^{V_{max}} \int_{n_{cmin}}^{n_{cmax}} f(V, n_c)\left(\frac{n_c^\alpha}{V^\beta}\right) dV dn_c \qquad (3)$$

In some implementations, the integration over the pore volumes and coordination numbers is approximated by a sum over the set of pores, where $V_j$ and $n_{c,j}$ represent the pore volume and connectivity number of a given pore j.

$$Z_{XRCT}(\alpha, \beta) \approx \sum_j \left(\frac{n_{c,j}^\alpha}{V_j^\beta}\right) \qquad (4)$$

After construction of the model for a controlled release device, the calibration parameters can be determined by the calibration module 330. In some implementations, the experimental data used for calibrating a minimalistic model for a class of controlled release devices includes a set of samples each including an experimentally determined release coefficient k and XRCT data (XRCT imagery or the set of minimalistic model extracted data 500) for a different controlled release device in the class. The calibration parameters α and β can be determined based on the experimental release profile data using a "grid analysis" technique, using formal optimization, using an iterative solver, or by using any other suitable technique. To determine α and β using grid analysis according to some embodiments, a 2D grid of $(\alpha_i, \beta_j)$ is generated over an expected range of values. Then, for each combination of $\alpha_i$ and $\beta_j$ in the grid, a corresponding model can be determined using a linear regression on Equation 2 to select the optimal values of the regression coefficients a and b given the selected values of $\alpha_i$ and $\beta_j$ and the experimental data (for each of which a corresponding $Z_{XRCT}(\alpha_i, \beta_j)$ value can be determined based on the XRCT data associated with each sample using Equation 4). Then, the combination of $\alpha_i$ and $\beta_j$ producing the lowest error (for example, the lowest squared error) are selected as the calibrated α and β for the model. In the grid analysis process a and b can also be determined as the regression coefficients of the linear regression. In other embodiments a formal optimization or other techniques can be used to determine α and β using similar calibration data.

Figure 6B:
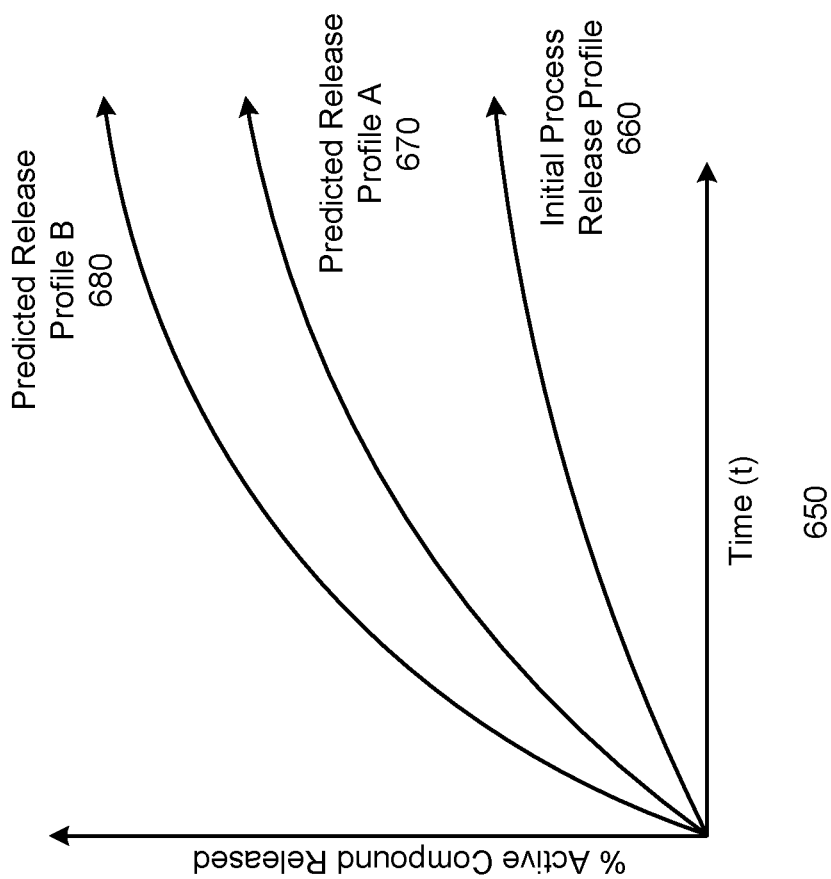
FIG. 6B is a graph illustrating example release profiles generated using a minimalistic model, according to one embodiment.
Figure 6A:
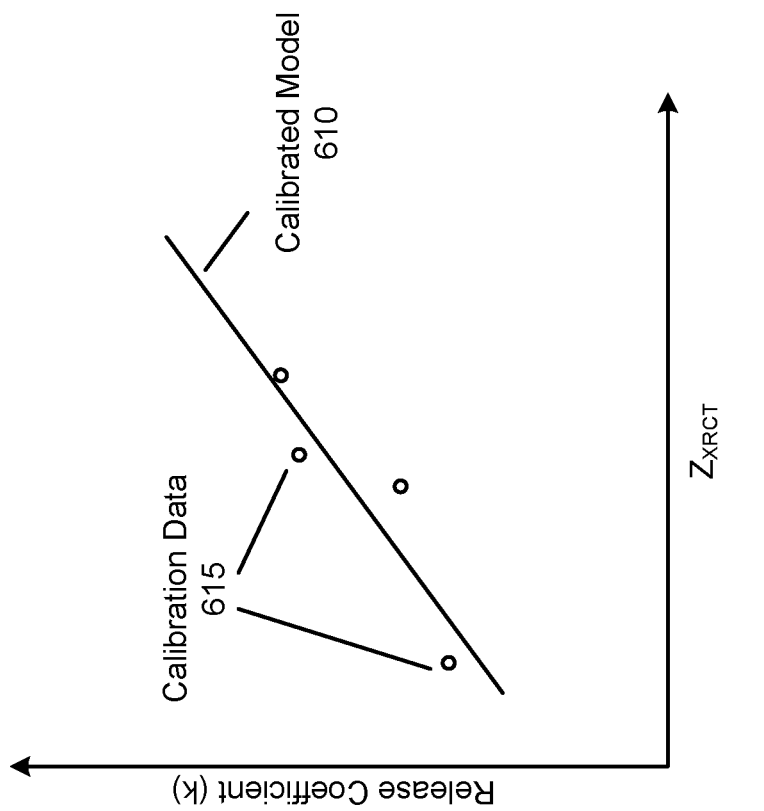
FIG. 6A is a graph illustrating an example calibrated model, according to one embodiment.

FIG. 6A is a graph illustrating an example calibrated model, according to one embodiment. The graph 600 of FIG. 6A illustrates the correlation between release coefficient k and $Z_{XRCT}$ in a calibrated model 610 as well as a set of calibration data 615 used to select the parameters of the calibrated model 610.

In some embodiments, the calibrated model (including, for example Equations 2 and 4 with the calibrated values of a, b, α, and β) can then be stored in the model store 255 for later use. FIG. 6B is a graph illustrating example release profiles generated using a minimalistic model, according to one embodiment. The graph 650 of FIG. 6B graphs a percentage of active compound released over time for an initial released profile 660 (for example, for a controlled release device used to generate the model), and predicted release profiles A and B 670 and 680 predicted based on the generated model. As described above, a release coefficient k for a controlled release device can be determined based on XRCT imagery of the device and a calibrated model for an appropriated class of controlled release devices.

The calibrated minimalistic models can be used to predict a release coefficient k and a corresponding release profile (for example, a Higuchi release profile based on Equation 1) predicting what percentage of the active compound will be released at a given time for a given controlled release device. In some implementations, the determined release coefficient k is used with an additional macroscopic model to predict additional characteristics of the controlled release device. For example, a macroscopic model can be used to predict the concentration profile (concentration of active compound as function of position within the controlled release device), interface dissolution front (the position of the "front" of undissolved active compound within the controlled release device), or as an alternative method of predicting release profile. A macroscopic model can be an Ordinary Differential Equation (ODE) system modeling a "front" of active compound (modeled as a circle for a cross section of a cylindrical controlled release device) with a decreasing radius as the active compound diffuses. In some implementations, the macroscopic model is based on an effective diffusivity $D_{e\!f\!f}$ which is proportional to the $Z_{XRCT}$ of the calibrated model.

In some embodiments, the micro-resolution network model 320 constructs network models predicting the release profile of a class of controlled release devices based on extracted XRCT features while maintaining a pore topology and the connections between pores in the controlled release device. The micro-resolution network model 320 can generate a network model based on data extracted from XRCT imagery of a controlled release device, as shown in FIG. 5. The network model extracted data 550 used to generate a network model can include a pore location, pore volume and connectivity matrix for each pore 460-480 of the segmented mask 450. In some implementations, network models generated by the micro-resolution network model 320 are generated based on network model extracted data 550 that lacks neck radius or other nanoscale features that cannot be extracted from the XRCT data. Therefore, the network models generated by the micro-resolution network model 320 are "micro-resolution" network models omitting nanoscale features (for example, neck radius).

In some implementations, the micro-resolution network model 320 analyzes only a fraction of the controlled release device assuming a consistent microstructure across the controlled release device, although other embodiments may analyze any amount of the controlled release device. The analyzed segment (herein, a "virtual implant") is treated as a discrete implant with the regions on the edges of the virtual implant assumed to be boundary pores connected to the external medium (providing an interface for the active compound to diffuse through). In some implementations, the virtual implant is sized to include a statistically significant number of boundary pores to prevent artificial resistance to diffusion.

The network of pores can be modeled as a set of nodes, each representing a pore (or domain) and connected to other pores of the network. In some implementations, each node is associated with a pore volume V and connected to other nodes (according to the connectivity matrix) by connections, each with a length D, for example measured based on the positions of the start and end nodes. The network can model the "moving boundary problem" of diffusing active compound by categorizing each node of the network as either a "dissolving node" still containing solid (undissolved) active compound, an "open node" containing only dissolved active compound (though potentially at a higher than ambient concentration), and a "boundary node" connected to the exterior, with an ambient concentration of dissolved active compound. The resulting network is simulated (integrated) until all active compound in nodes connected to the boundary nodes is dissolved, recording the total amount dissolved as a function of time (the function $W_{ntw}(t)$). Then, Equation 1 (shown above) can be used to determine a preliminary release constant $K_{ntw}$ by fitting the simulated $K_{ntw}(t)$ to Equation 1. In some implementations, the resulting preliminary release constant $K_{ntw}$ is further calibrated by the calibration module 330 (for example, using experimental data) to find the calibration coefficients c and d.

$$k = cK_{ntw} + d \tag{5}$$

The resulting calibrated network model can be stored in the model store 255 and used to predict a release coefficient k or other suitable characteristics.

Implant Modeling System Application

Figure 7:
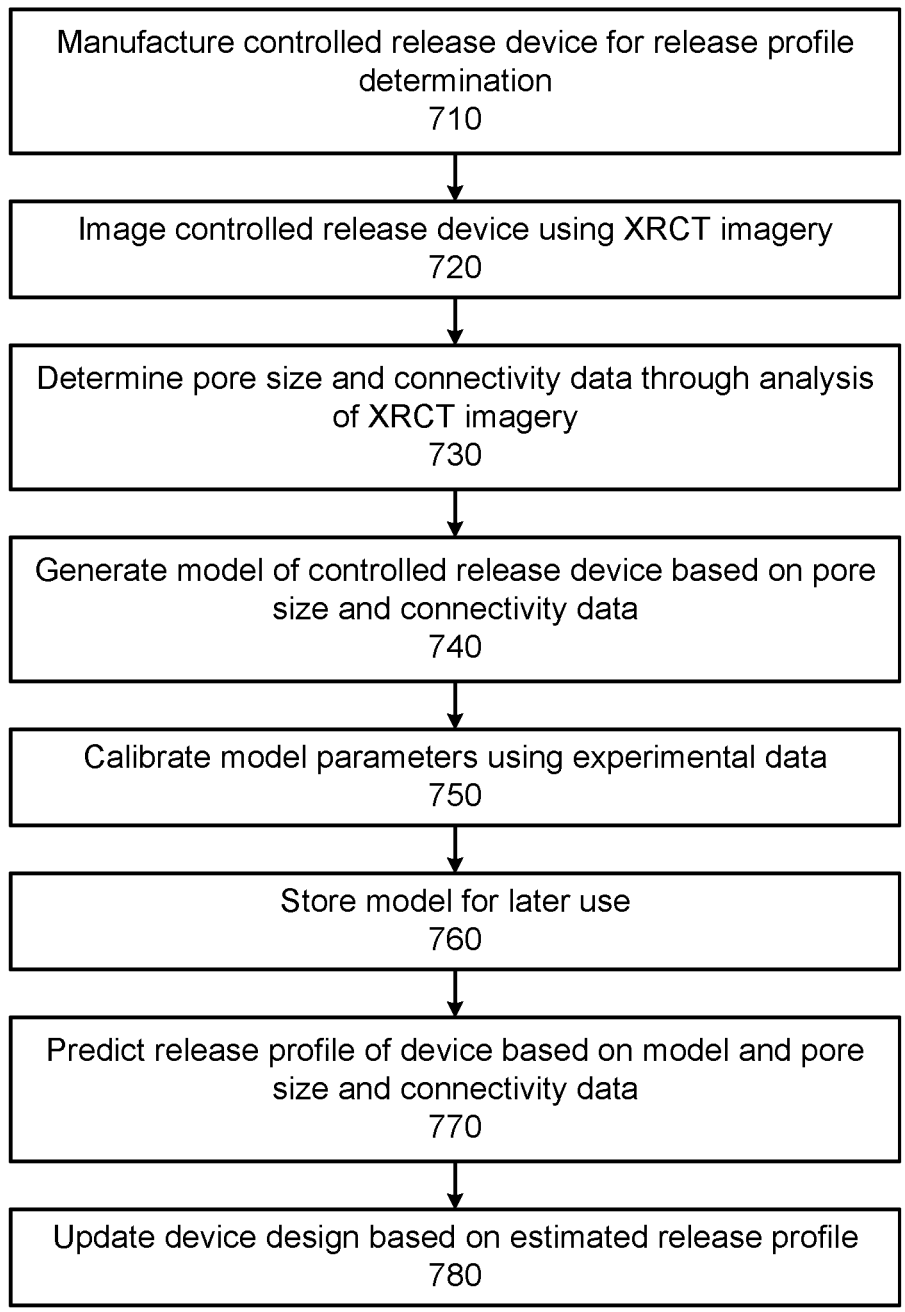
FIG. 7 is a flowchart illustrating an example process for generating and calibrating a model based on XRCT imagery of controlled release device, according to one embodiment.

FIG. 7 is a flowchart illustrating an example process for generating and calibrating a model based on XRCT imagery of controlled release device, according to one embodiment. The process 700 of FIG. 7 begins with the manufacture 710 of a controlled release device to be tested. For example, the controlled release device can be a prototype medical implant with an unknown release profile. Then, the controlled release device can be imaged 720 using XRCT imagery or another suitable imaging technology. Based on analysis of the XRCT imagery, pore size and connectivity data for the controlled release device can be determined 730. Using the pore size and connectivity data, a model of the controlled release device is generated 740. For example, a minimalistic model can be generated based on pore size and a connectivity number for each of a plurality of pores of a controlled release device. Using experimental data, the parameters of the model are calibrated 750 and the calibrated model can be stored 760 for later use. Using the stored model and pore size and connectivity data the release profile (or other characteristics) of the controlled release device is predicted 770. The design of the controlled release device can then be updated 780 based on the estimated release profile or other characteristics.

Figure 8:
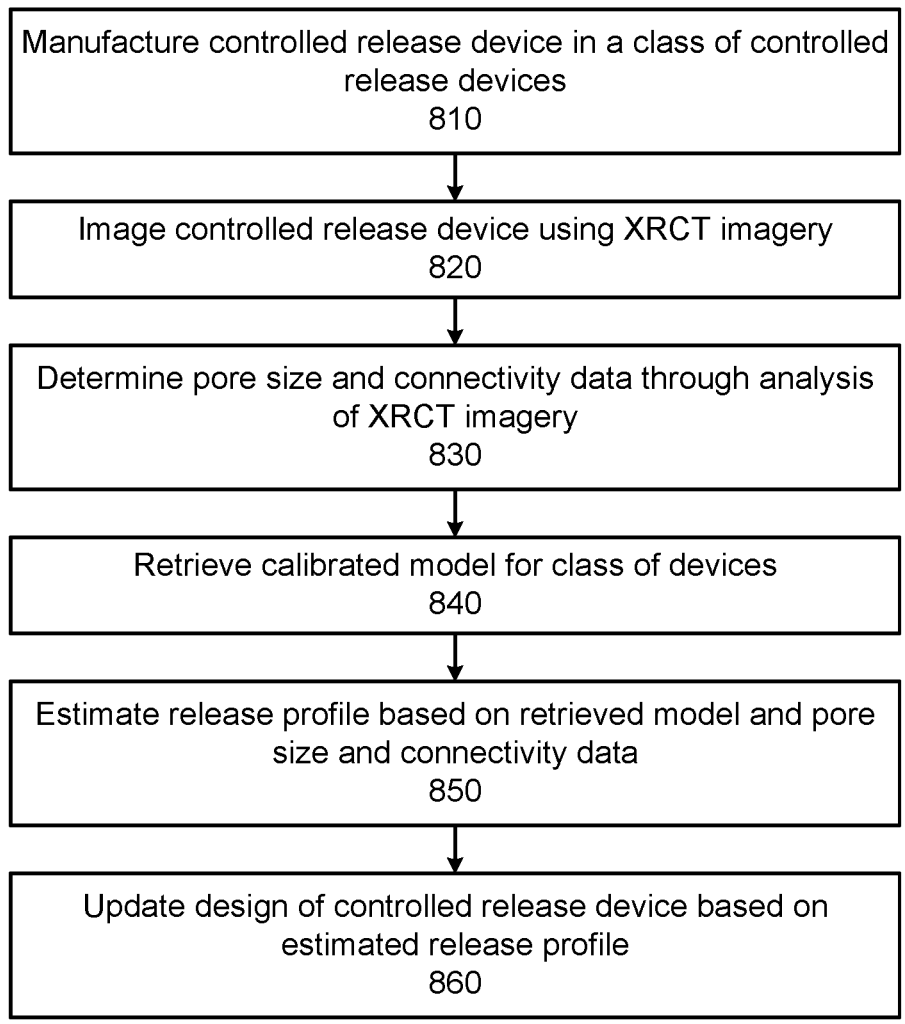
FIG. 8 is a flowchart illustrating an example process for predicting the release profile of controlled release device based on a model and XRCT imagery of the device, according to one embodiment.

FIG. 8 is a flowchart illustrating an example process for predicting the release profile of controlled release device based on a model and XRCT imagery of the device, according to one embodiment. The process 800 of FIG. 8 begins with the manufacture 810 of a controlled release device to be tested, where the controlled release device belongs to a class of controlled release devices. The controlled release device can then be imaged 820 using XRCT or another suitable imaging technology, and based on analysis of the XRCT imagery pore size and connectivity data of the controlled release device determined 830. A model (for example, a pre-calibrated model) for the class of controlled release devices containing the controlled release device to be tested can then be retrieved 840. Using the retrieved model and the XRCT data, the release profile for the controlled release device is estimated 850. Based on the estimated release profile, the design of the controlled release device can be updated 860.

Figure 9:
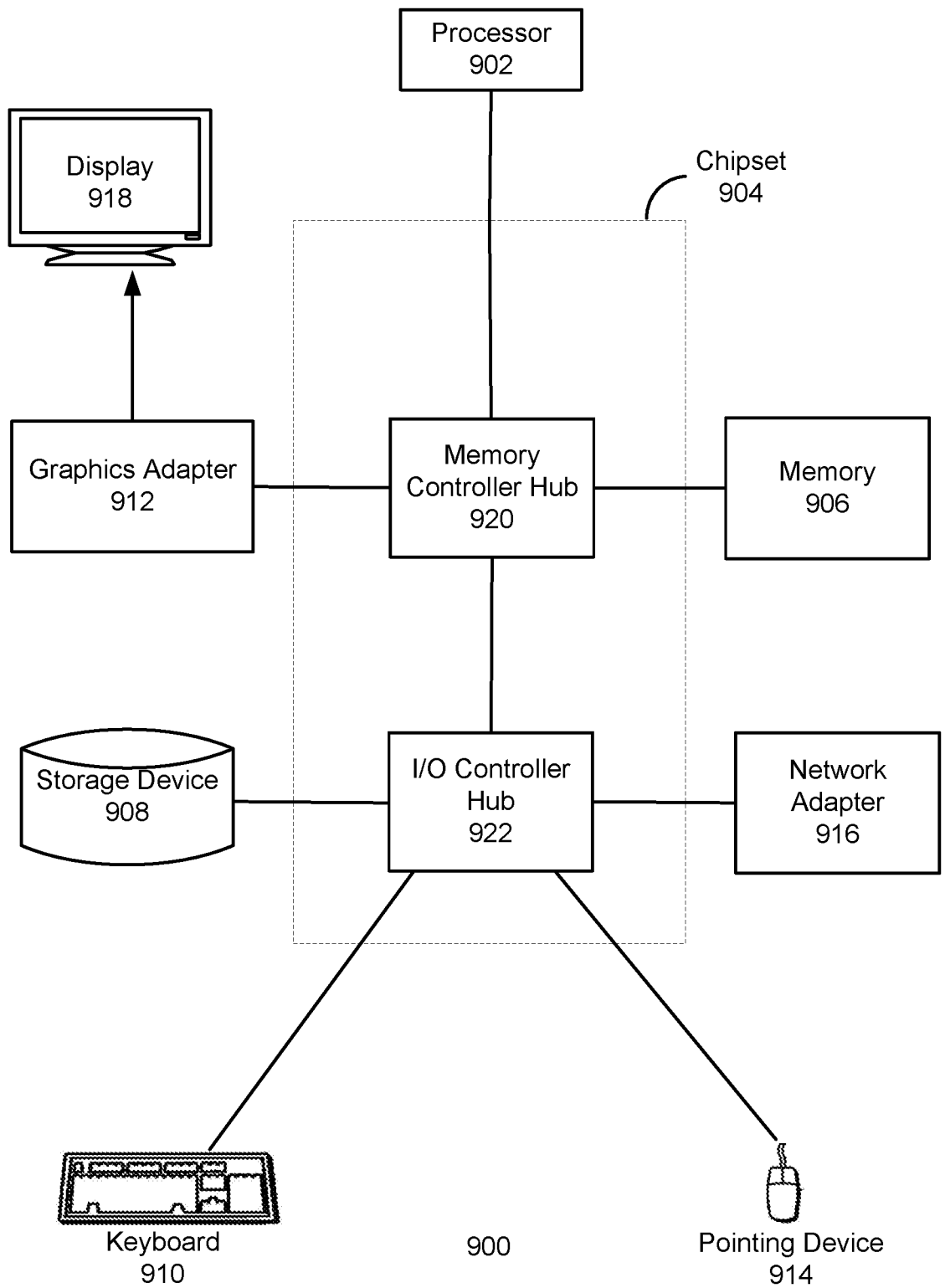
FIG. 9 illustrates an example computer system for implementing an implant modeling system, according to one embodiment.

FIG. 9 illustrates an example computer system for implementing an implant modeling system, according to one embodiment. The computer 900 includes at least one processor 902 coupled to a chipset 904. The chipset 904 includes a memory controller hub 920 and an input/output (I/O) controller hub 922. A memory 906 and a graphics adapter 912 are coupled to the memory controller hub 920, and a display 918 is coupled to the graphics adapter 912. A storage device 908, an input device 914, and network adapter 916 are coupled to the I/O controller hub 922. Other embodiments of the computer 900 have different architectures.

The storage device 908 is a non-transitory computer-readable storage medium such as a hard drive, compact disk read-only memory (CD-ROM), DVD, or a solid-state memory device. The memory 906 holds instructions and data used by the processor 202. The input interface 914 is a touch-screen interface, a mouse, track ball, or other type of pointing device, a keyboard, or some combination thereof, and is used to input data into the computer 900. In some embodiments, the computer 900 may be configured to receive input (e.g., commands) from the input interface 914 via gestures from the user. The graphics adapter 912 displays images and other information on the display 918. The network adapter 916 couples the computer 900 to one or more computer networks.

The computer 900 is adapted to execute computer program modules for providing functionality described herein. As used herein, the term "module" refers to computer program logic used to provide the specified functionality. Thus, a module can be implemented in hardware, firmware, and/or software. In one embodiment, program modules are stored on the storage device 908, loaded into the memory 906, and executed by the processor 902.

The types of computers 900 used by the entity of FIG. 1 can vary depending upon the embodiment and the processing power required by the entity. For example, the implant modeling system 220 can run in a single computer 900 or multiple computers 900 communicating with each other through a network, such as in a server farm. The computers 900 can lack some of the components described above, such as graphics adapters 912, and displays 918.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Any terms not directly defined herein shall be understood to have the meanings commonly associated with them as understood within the art. Certain terms are discussed herein to provide additional guidance to the practitioner in describing the compositions, devices, methods and the like disclosed, and how to make or use them. It will be appreciated that the same thing may be said in more than one way. Consequently, alternative language and synonyms may be used for any one or more of the terms discussed herein. No significance is to be placed upon whether or not a term is elaborated or discussed herein. Some synonyms or substitutable methods, materials and the like are provided. Recital of one or a few synonyms or equivalents does not exclude use of other synonyms or equivalents, unless it is explicitly stated. Use of examples, including examples of terms, is for illustrative purposes only and does not limit the scope and meaning of the disclosure.

It must be noted that, as used in the specification, the singular forms "a," "an" and "the" include plural referents unless the context clearly dictates otherwise.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may include a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Embodiments of the invention may also relate to a computer data signal embodied in a carrier wave, where the computer data signal includes any embodiment of a computer program product or other data combination described herein. The computer data signal is a product that is presented in a tangible medium or carrier wave and modulated or otherwise encoded in the carrier wave, which is tangible, and transmitted according to any suitable transmission method.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A computer-implemented method for estimating a release profile of a device for releasing a compound, the method comprising:
   receiving an x-ray computed tomography (XRCT) image of the device, the device comprising particles of the compound embedded in a plurality of pores in a matrix;
   generating an unlabeled mask from the XRCT image, the unlabeled mask identifying pores and necks connecting a set of the pores;
   performing an erosion process on the unlabeled mask to generate an eroded mask, the erosion process eroding the pores and removing the necks connecting the set of the pores resulting in disconnected pores;
   labeling the disconnected pores in the eroded mask;
   performing a dilation process on the eroded mask to generate a dilated mask, the dilation process enlarging the labeled pores that were previously eroded and unlabeled;
   extracting, from the dilated mask, a set of features including pore volumes and connectivities for the labeled pores;
   retrieving a minimalistic model for estimating the release profile of the device based on the pore volume and connectivity, wherein the minimalistic model determines a correlation between a release coefficient for a Higuchi-type release and an XRCT parameter, wherein the XRCT parameter is based on the pore volumes and connectivities;
   and estimating the release profile of the device based on the correlation determined using the retrieved minimalistic model and the pore volumes and connectivities.

2. The computer-implemented method of claim 1, wherein the XRCT image is a voxel-based virtual 3D model of the device with a maximum resolution of one micron.

3. The computer-implemented method of claim 1, wherein the connectivity for a given pore is a connectivity number representing a number of other pores the given pore is connected to.

4. The computer-implemented method of claim 1, wherein the connectivities are a connectivity matrix identifying other pores that each pore of the labeled pores is connected to.

5. The computer-implemented method of claim 1, further comprising:
   constructing, based on the pore volumes and connectivities, an initial minimalistic model of the device and calibrating the initial minimalistic model,
   wherein the retrieving of the minimalistic model for estimating the release profile of the device comprises retrieving the calibrated minimalistic model.

6. The computer-implemented method of claim 1, further comprising adjusting one or more parameters of a process for manufacturing the device based on the estimated release profile.

7. The computer-implemented method of claim 1, wherein the device is a controlled release implant and the compound is an active pharmaceutical ingredient.

8. A system for estimating a release profile of a device for releasing a compound, the system comprising:
   an x-ray computed tomography (XRCT) imaging system configured to capture an XRCT image of the device, the device comprising particles of the compound embedded in a plurality of pores in a matrix;
   at least one processor;
   and a non-transitory computer readable medium comprising stored instructions, the instructions when executed by the at least one processor cause the at least one processor to:
   generate an unlabeled mask from the XRCT image, the unlabeled mask identifying pores and necks connecting a set of the pores;
   perform an erosion process on the unlabeled mask to generate an eroded mask, the erosion process eroding the pores and removing the necks connecting the set of the pores resulting in disconnected pores;
   label the disconnected pores in the eroded mask;

perform a dilation process on the eroded mask to generate a dilated mask, the dilation process enlarging the labeled pores that were previously eroded and unlabeled;

extract, from the dilated mask, a set of features including pore volumes and connectivities for the labeled pores;

retrieve a minimalistic model for estimating the release profile of the device based on the pore volume and connectivity, wherein the minimalistic model determines a correlation between a release coefficient for a Higuchi-type release and an XRCT parameter, wherein the XRCT parameter is based on the pore volumes and connectivities;

and estimate the release profile of the device based on the correlation determined using the retrieved minimalistic model and the pore volumes and connectivities.

9. The system of claim 8, wherein the XRCT image is a voxel-based virtual 3D model of the device with a maximum resolution of one micron.

10. The system of claim 8, wherein the connectivity for a given pore is a connectivity number representing a number of other pores the given pore is connected to.

11. The system of claim 8, wherein the connectivities are a connectivity matrix identifying the other pores each pore of the labeled pores is connected to.

12. The system of claim 8, wherein the instructions when executed bythe at least one processor further cause the at least one processor to:

construct, based on the pore volumes and connectivities, an initial minimalistic model of the device and calibrate the initial minimalistic model, wherein the retrieval of the minimalistic model for estimating the release profile of the device comprises retrieving the calibrated minimalistic model.

13. The system of claim 8, wherein the instructions when executed by the at least one processor further cause the at least one processor to adjust one or more parameters of a process for manufacturing the device based on the estimated release profile.

14. The system of claim 8, wherein the device is a controlled release implant and the compound is an active pharmaceutical ingredient.

15. A non-transitory computer-readable medium comprising instructions for estimating a release profile of a device for releasing a compound, the instructions, when executed by a computing system, causing the computing system to perform operations including:

receiving an x-ray computed tomography (XRCT) image of the device, the device comprising particles of the compound embedded in a plurality of pores in a matrix;

generating an unlabeled mask from the XRCT image, the unlabeled mask identifying pores and necks connecting a set of the pores;

performing an erosion process on the unlabeled mask to generate an eroded mask, the erosion process eroding the pores and removing the necks connecting the set of the pores resulting in disconnected pores;

labeling the disconnected pores in the eroded mask;

performing a dilation process on the eroded mask to generate a dilated mask, the dilation process enlarging the labeled pores that were previously eroded and unlabeled;

extracting, from the dilated mask, a set of features including pore volumes and connectivities for the labeled pores;

retrieving a minimalistic model for estimating the release profile of the device based on the pore volume and connectivity, wherein the minimalistic model determines a correlation between a release coefficient for a Higuchi-type release and an XRCT parameter, wherein the XRCT parameter is based on the pore volumes and connectivities;

and estimating the release profile of the device based on the correlation determined using the retrieved minimalistic model and the pore volumes and connectivities.

16. The non-transitory computer-readable medium of claim 15, wherein the XRCT image is a voxel-based virtual 3D model of the device with a maximum resolution of one micron.

17. The non-transitory computer-readable medium of claim 15, wherein the connectivity for a given pore is a connectivity number representing a number of other pores the given pore is connected to.

18. The non-transitory computer-readable medium of claim 15, wherein the connectivities are a connectivity matrix identifying other pores that each pore of the labeled pores is connected to.

19. The non-transitory computer-readable medium of claim 15, wherein the operations further include:

constructing, based on the pore volumes and connectivities, an initial minimalistic model of the device;

and calibrating the initial minimalistic model, wherein the retrieving of the minimalistic model for estimating the release profile of the device comprises retrieving the calibrated minimalistic model.

20. The non-transitory computer-readable medium of claim 15, wherein the operations further include adjusting one or more parameters of a process for manufacturing the device based on the estimated release profile.

* * * * *